(12) United States Patent
Kawai et al.

(10) Patent No.: US 6,472,575 B2
(45) Date of Patent: Oct. 29, 2002

(54) PROCESS FOR PRODUCING ADAMANTANE

(75) Inventors: Takeshi Kawai, Tsukuba (JP); Wataru Ueno, Tsukuba (JP); Ryuuji Fujiura, Tsukuba (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 09/874,068

(22) Filed: Jun. 6, 2001

(65) Prior Publication Data

US 2001/0051755 A1 Dec. 13, 2001

(30) Foreign Application Priority Data

Jun. 13, 2000 (JP) ........................................ 2000-176725

(51) Int. Cl.$^7$ .............................................. C07C 13/28
(52) U.S. Cl. ...................................................... 585/352
(58) Field of Search ........................................ 585/352

(56) References Cited

U.S. PATENT DOCUMENTS 3,356,751 A * 12/1967 Schneider ................... 585/352

OTHER PUBLICATIONS

Database WPI, Section Ch., Week 197532, Derwent Publications Ltd., London, GB; AN 1975–53041W XP002186941—Abstract of JP 50–035151.

Patent Abstracts of Japan, vol. 010, No. 120 (C–343), May 6, 1986—Abstract of JP 60–246333.

* cited by examiner

*Primary Examiner*—Thuan D. Dang
(74) *Attorney, Agent, or Firm*—Wenderoth, Lind & Ponack, L.L.P.

(57) ABSTRACT

A process for producing adamantane (tricyclodecane [$3.3.1.1^{3,7}$]) by isomerization reaction of tetrahydrodicyclopentadiene (tricyclodecane[$5.2.1.0^{2,6}$]) with a $HF.BF_3$ catalyst, wherein the reaction is carried out in the presence of at least one metal selected from the group consisting of the group 8 metals, the group 9 metals and the group 10 metals of the periodic table and hydrogen, which process can give an intended adamantane at a high selection rate.

4 Claims, No Drawings

PROCESS FOR PRODUCING ADAMANTANE

FIELD OF THE INVENTION

The present invention relates to a process for producing adamantane (tricyclodecane[3.3.1.1$^{3,7}$]) by isomerization reaction of tetrahydrodicyclopentadiene (tricyclodecane [5.2.1.0$^{2,6}$]) with a HF.BF$_3$ catalyst. Adamantane is a very useful raw material for producing an adamantane derivative and is applied to specialty chemical and fine chemical fields including a druggery, special fuel, a lubricant, an engineering polymer, a functional polymer, an agrichemical and a surfactant.

PRIOR ART OF THE INVENTION

Generally, adamantane is obtained by isomerization of tetrahydrodicyclopentadiene. Conventionally, as a catalyst used for producing adamantane, there are known aluminum halide type catalysts, alumina type catalysts, zeolite type catalysts and superacid catalysts.

When the aluminum halide type catalyst such as AlCl$_3$-HCl, AlBr$_3$-t-BuBr, AlCl$_3$-t-BuCl is used, the amount of the catalyst based on a raw material is required to increase. Further, a byproduct compound formed by the reaction is apt to form a strong complex with the catalyst. Therefore, defects are that an activity decreases immediately and that the renewal of the catalyst is difficult. Journal of Brennst-Chem. 1961, 42, 90, describes a method in which a reaction is carried out by using HCl-AlCl$_3$ catalyst under high hydrogen pressure. In this system, high pressure hydrogen is required and many problems are found with regard to the recovering method of a catalyst.

Further, alumina support catalysts such as chlorinated platinum - alumina and sulfuric acid-treated silica - alumina have a low activity and the lifetime of these catalysts is short.

As a method of highly selectively obtaining adamantane, conventional methods include the use of a rare earth element-exchanged zeolite catalyst, trifluoromethanesulfonic acid (CF$_3$SO$_3$H), trifluoromethanesulfonic acid-antimony pentafluoride (CF$_3$SO$_3$H+SbF$_5$), trifluoromethylsulfonylboron (B(OSO$_2$CF$_3$)$_3$) and the like.

For example, JP-A-60-246333 discloses a method in which a cation exchange zeolite supporting an active metal such as platinum is used. In this method, an active metal is used as an isomerization catalyst, and when the unmodified zeolite supporting an active metal is used, a ring opening reaction by hydrogenation occurs so that a treatment with ammonium sulfate or the like is required, i.e., a preparation method is complicated. With regard to reaction results, the selection rate is low or approximately 50%, and the yield is low or approximately 40%.

Further, the use of a catalyst such as CF$_3$SO$_3$H+SbF$_5$ or CF$_3$SO$_3$H+B(OSO$_2$CF$_3$)$_3$ described in J.org. Chem., 1986, 51, 5410–5413, can give adamantane highly selectively, while the problem is that the handling and recovery of a catalyst are difficult.

On the other hand, when a HF.BF$_3$ type catalyst which is a kind of superacid catalyst is used, it is known that adamantane can be obtained at a high yield of 60% or higher as proposed, for example, in JP-A-50-35151.

The HF.BF$_3$ type catalyst is excellent in handling properties and recovery of a catalyst and can give adamantane at high yields. However, the selection rate of adamantane is approximately 60 to 75%. In a process using a superacid such as a HF.BF$_3$ type catalyst, a high cost is required for separation and purification so that an increase in selectivity is highly advantageous. It is desired to increase the selectivity further.

SUMMARY OF THE INVENTION

It is an object of the present invention to provide a process for producing adamantane (tricyclodecane[3.3.1.1$^{3,7}$]) by isomerization reaction of tetrahydrodicyclopentadiene (tricyclodecane[5.2.1.0$^{2,6}$]) with a HF.BF$_3$ catalyst which process gives an intended adamantane at a high selection rate.

That is, the present invention is directed to a process for producing adamantane (tricyclodecane [3.3.1.1$^{3,7}$]) by isomerization reaction of tetrahydrodicyclopentadiene (tricyclodecane[5.2.1.0$^{2,6}$]) with a HF.BF$_3$ catalyst, which process is characterized in that the reaction is carried out in the presence of at least one metal selected from the group consisting of the group 8 metals, the group 9 metals and the group 10 metals of the periodic table and hydrogen.

DETAILED DESCRIPTION OF THE INVENTION

The present inventors have made diligent studies for overcoming the above problems and have found that at least one metal selected from the group consisting of the group 8 metals, the group 9 metals and the group 10 metals of the periodic table is added to an isomerization reaction system with a HF.BF$_3$ catalyst under a reduction atmosphere, whereby adamantane can be highly selectively produced at high yields. On the basis of the above finding, the present invention is reached.

The metal used in the present invention is at least one metal selected from the group consisting of the group 8 metals, the group 9 metals and the group 10 metals of the periodic table, such as Fe, Co, Ni, Cu, Ru, Pd, Ir and Pt. In particular, palladium, platinum and nickel may be preferably used. For preferable uses thereof, these metals may be on a support. Preferable examples include platinum/activated carbon, palladium/activated carbon, or the like.

The reaction conditions of the present invention are as follows. 0.5 to 10 parts by weight, preferably 3 to 4.5 parts by weight, of HF, 0.25 to 1.5 parts by weight, preferably 0.5 to 1.3 parts by weight, of BF$_3$ and 0.0001 to 0.001 part by weight, preferably 0.0003 to 0.0007 part by weight, of the above metal are used per 1 part of tetrahydrodicyclopentadiene. Further, hydrogen is used so as to achieve a partial pressure of 0.1 to 5.0 Mpa, preferably 0.5 to 2.0 Mpa, whereby a reduction atmosphere is obtained. The reaction temperature is 0 to 120° C., preferably 40 to 80° C. The reaction pressure is 0.6 to 7.0 Mpa, preferably 1.1 to 3.5 Mpa.

EXAMPLES

The present invention will be explained more in detail with reference to Examples hereinafter, while the present invention shall not be limited to the following Examples.

Example 1

18 g of tetrahydrodicyclopentadiene, 0.15 g of 5 wt % platinum/activated carbon, and 80 g of HF were placed in a 300 ml-autoclave equipped with a magnetic stirrer, a baffle plate, a gas-introducing opening and a liquor-feeding opening and made of Hastelloy, and 23 g of BF$_3$ was introduced to the autoclave. Then, hydrogen was introduced to the autoclave so as to achieve a partial pressure of 1.5 Mpa, the contents in the autoclave was heated by feeding hot water to the outside (jacket) of the autoclave with stirring, and the liquid temperature in the autoclave was increased up to 50° C. with stirring. After 45 minutes from the reaching of the liquid temperature to 50° C., the stirring was terminated and the contents in the autoclave were allowed to stand to complete the reaction. After the completion of the reaction, the reaction liquor was drawn from the bottom of the reactor and diluted with water. An organic substance in the catalyst layer was extracted with hexane and analyzed by a gas chromatography. The conversion rate of tetrahydrodicyclopentadiene was 87.3%. The adamantane selection rate was 88.2%.

Example 2

Example 1 was repeated except that the 5 wt % platinum/activated carbon was replaced with 5 wt % palladium/activated carbon. The conversion rate of tetrahydrodicyclopentadiene was 89.7%. The adamantane selection rate was 83.6%.

Comparative Example 1

Example 1 was repeated except that the 5 wt % platinum/activated carbon was not used. The conversion rate of tetrahydrodicyclopentadiene was 93.2%. The adamantane selection rate was 57.2%.

EFFECT OF THE INVENTION

According to the present invention, adamantane can be obtained at a high selection rate at high yields when adamantane is produced by isomerization reaction of tetrahydrodicyclopentadiene with a $HF \cdot BF_3$ catalyst.

What is claimed is:

1. A process for producing adamantane (tricyclodecane [$3.3.1.1^{3,7}$]) by isomerization reaction of tetrahydrodicyclopentadiene (tricyclodecane[$5.2.1.0^{2,6}$]) with a $HF \cdot BF_3$ catalyst, wherein the reaction is carried out in the presence of at least one metal selected from the group consisting of the group 8 metals, the group 9 metals and the group 10 metals of the periodic table and hydrogen.

2. A process according to claim 1, wherein the metal selected from the group consisting of the group 8 metals, the group 9 metals and the group 10 metals of the periodic table is Fe, Co, Ni, Cu, Ru, Pd, Ir or Pt.

3. A process according to claim 1, wherein the adamantane is produced by incorporating 0.5 to 10 parts by weight of HF, 0.25 to 1.5 parts by weight of $BF_3$, and 0.0001 to 0.001 part by weight of the metal selected from the group consisting of the group 8 metals, the group 9 metals and the group 10 metals of the periodic table per 1 part by weight of tetrahydrodicyclopentadiene.

4. A process according to claim 1, wherein the reaction is carried out at a hydrogen partial pressure of 0.1 to 5.0 Mpa at a reaction temperature of 0 to 120° C. under a reaction pressure of 0.6 to 7.0 Mpa.

* * * * *